(12) United States Patent
Kotani et al.

(10) Patent No.: US 7,736,678 B2
(45) Date of Patent: Jun. 15, 2010

(54) **METHOD OF ENHANCING BLOOD ANTIOXIDANT ACTIVITY INGESTING A COMPOUND IN THE FORM OF AT LEAST ONE FORM SELECTED FROM AMONGST JUICE, POWDER, GRANULE, TABLET AND CAPSULE, WHICH CONTAINS AN EFFECTIVE AMOUNT OF AT LEAST ONE VEGETABLE SELECTED FROM THE GROUP CONSISTING OF BROCCOLI, SPINACH, PARSLEY, *KOMATSUNA (BRASSICAD RAPA* L.) AND JAPANESE RADISH LEAVES, AND AT LEAST ONE VEGETABLE SELECTED FROM AMONGST LETTUCE, CABBAGE AND CELERY**

(75) Inventors: Mayumi Kotani, Kobe (JP); Akihito Fujita, Takatsuki (JP); Masahiro Matsuura, Takatsuki (JP); Taketoshi Makino, Settsu (JP)

(73) Assignee: Sunstar Inc., Osaka (JP)

( * ) Notice: Subject to any disclaimer, the term of this patent is extended or adjusted under 35 U.S.C. 154(b) by 55 days.

(21) Appl. No.: 10/537,339

(22) PCT Filed: Dec. 5, 2003

(86) PCT No.: PCT/JP03/15572

§ 371 (c)(1),
(2), (4) Date: Jun. 2, 2005

(87) PCT Pub. No.: WO2004/052385

PCT Pub. Date: Jun. 24, 2004

(65) Prior Publication Data

US 2006/0018983 A1    Jan. 26, 2006

(30) Foreign Application Priority Data

Dec. 6, 2002    (JP) ............................. 2002-354919
Apr. 4, 2003    (JP) ............................. 2003-101496

(51) Int. Cl.
*A61K 36/31*    (2006.01)
(52) U.S. Cl. ...................... 424/755; 424/774; 424/725
(58) Field of Classification Search ....................... None
See application file for complete search history.

(56) References Cited

U.S. PATENT DOCUMENTS 6,270,774 B1 *   8/2001   Hsia et al. .............. 424/195.11
6,344,214 B1 *   2/2002   Lorenz ....................... 424/451

FOREIGN PATENT DOCUMENTS

| JP | 61-112024 A | 5/1986 |
|---|---|---|
| JP | 04-008256 A | 1/1992 |
| JP | 06-199687 A | 7/1994 |
| JP | 09-009939 A | 1/1997 |
| JP | 10-276721 A | 10/1998 |
| JP | 11-001686 A | 1/1999 |
| JP | 2000-169382 A | 6/2000 |
| JP | 2000-198740 A | 7/2000 |
| JP | 2000-219880 A | 8/2000 |
| JP | 2000-229834 A | 8/2000 |
| JP | 2000-300224 A | 10/2000 |
| JP | 2001-270832 A | 10/2001 |
| JP | 2001-299305 A | 10/2001 |
| JP | 2002-068979 A | 3/2002 |
| JP | 2002-119265 A | 4/2002 |
| JP | 2002-153210 A | 5/2002 |
| JP | 2002-220340 A | 8/2002 |
| JP | 2002-226368 A | 8/2002 |
| JP | 2002-238536 A | 8/2002 |
| JP | 2002-275018 A | 9/2002 |
| JP | 2002-275076 A | 9/2002 |
| JP | 2002-308768 A | 10/2002 |
| JP | 2002-360205 A | 12/2002 |
| WO | WO 98/33494 | 8/1998 |

OTHER PUBLICATIONS

Rosso, J; Lukins, S. The New Basics Cookbook. Workman Publishing: New York, 1989. p. 94.*
Strain, J.J.; Elwood, P.C.; Davis, A. Kennedy, O.; Coulter, J.; Fehily, A.; Mulholland, C.W.; Robson, P.J.; and Thurnham, D.I. Euro. J. Clin. Nutr. 2000; 54: 828-833.*
Chambers (Food Chem. (1996), vol. 57, No. 2, pp. 271-274).*
English translation of JP 2002-226368—Aug. 2002.*
http://www.vplants.org/plants/species/species.jsp?gid=5442—accessed Jun. 25, 2009.*
Gabriella Gazzani, et al., "Anti-and Prooxidant Activity of Water Soluble Components of Some Common Diet Vegetables and the Effect of Thermal Treatment," J. Agric. Food Chem., 1998, vol. 46, No. 10, pp. 4118-4122.
Yi-Fang Chu, et al., "Antioxidant and Antiproliferative Activities of Common Vegetables," J. Agric. Food Chem., 2002, vol. 50, No. 23, pp. 6910-6916.
J. J. Jamora, et al., "Storage Stability of Extruded Products from Blends of Meat and Nonmeat Ingredients: Evaluation Methods and Antioxidative Effects of Onion, Carrot, and Oat Ingredients," J. Food Science, 2002, vol. 67, Nr. 5, pp. 1654-1659.

(Continued)

*Primary Examiner*—Susan C Hoffman
(74) *Attorney, Agent, or Firm*—Fitch, Even, Tabin & Flannery

(57) ABSTRACT

The present invention provides a composition comprising a green-yellow vegetable (e.g., broccoli, spinach, parsley, komatsuna (*Brassica rapa* L.), Japanese radish leaves) and a light-colored vegetable (e.g., lettuce, cabbage, celery), the composition having the following effects:
(1) inhibiting the generation of blood lipid peroxide;
(2) lowering blood TBARS levels or suppressing the elevation of blood TBARS levels;
(3) increasing blood vitamin E levels;
(4) enhancing blood antioxidant activity;
(5) enhancing blood TRAP levels;
(6) lowering blood active oxygen levels or suppressing the elevation of blood active oxygen levels; and
(7) preventing or treating diabetic complications.

3 Claims, 3 Drawing Sheets

OTHER PUBLICATIONS

Achim Bub et al., "Moderate Intervention with Carotenoid-Rich Vegetable Products Reduces Lipid Peroxidation in Men," J. Nutrition, 2000, vol. 130, No. 9, pp. 2200-2206.

Anne C. Kurilich et al., "Carotene, Tocopherol, and Ascorbate Contents in Subspecies of *Brassica oleracea*," J. Agric Food Chem., 1999, vol. 47, No. 4, pp. 1576-1581.

D. Mark Hodges, et al., "Improving the Thiobarbituric Acid-Reactive-Substances Assay for Estimating Lipid Peroxidation in Plant Tissues Containing Anthocyanin and Other Interfering Compounds," Planta, 1999, vol. 207, No. 4, pp. 604-611.

Masaki Tokuda et al., "Kajitsu, Yasai O Genryo to Shita Kako, Oita Nosuisanbutsu Kako Sogo Sido, Center Shiken Seiseki Hokikusyo," 1997, vol. 19996, pp. 5-8.

Sukie Nishibori et al., "Superoxide Anion Radical-Scaveging Ability of Freshi and Heated Vegetable Juices,"Nippon Shokuhin Kagaku Kogaku Kaishi, 1998, vol. 45, No. 2, pp. 144-148.

Huifeng Ren, et al., "Antioxidative and Antimicrobial Activities and Flavonoid Contents of Organically Cultivated Vegetables," Nippon Shokuhin Kagaku Kogaku Kaishi, 2001, vol. 48, No. 4, pp. 246-252.

Tomoni Akutsu et al., "Shokuhin Kaikibutsu O Mochiita Kinosei Shokuhin Sozai No Kaihatsu—Shokuhin Haikbutsuto Kara No Kinosei No Kenseku -, Shokuhin Kogyo Shidosho Kenkyu Hokoku," 2002, vol. 16. pp. 4-9.

Tadashi Kato et al., "Increases of Various Vitamin Contents in Leaf Vegetables Treated by the Winter-Cool Air," Tohoku Agricultural Research, 1994, vol. 47, pp. 317-318.

Yaeko Izaki et al., "Ryokuoushoku Yasai Ni Okeru Chlorophyll Carotene Tocophenol Kanyuryo Narabini Sokan Ni Tsuite," Kyotofu Eisei Kenkyu Nenpo, 1986, No. 52, pp. 69-71.

Suido et al., A mixed green vegetable and fruit beverage decreased the serum level of low-intensity lipoprotein cholesterol in hyperchloesterolemic patients, Journal of Agriculture and Food Chemistry, 50(11):336-3350 (2002).

Terao "Dietary flavonoids as antioxidants in vivo: Conjugated metabolites of (−)-epicatechin and quercetin participate in antioxidative defense in blood plasma." Journal of Medical Investigation (1999), vol. 46, No. 314, pp. 159-168.

Nielson, et al. "Effect of parsley (Petroselinum crispum) intake on urinary apigenin excretion, blood antioxidant enzymes and biomarkers for oxidative stress in human subjects." British Journal of Nutrition (1999), vol. 81, No. 6, pp. 447-455.

Nakamura et al. "Research on function and physiology of natural phenolic antioxidant." (2001), No. 118, pp. 185-192.

Niwa "Antioxidant activities of natural plants and vegetable soup." Medicine and Biology (1995), vol. 131, No. 5, pp. 215-220.

Cao et al. "Serum Antioxidant Capacity is Increased by Consumption of Strawberries, Spinach, Red Wine or Vitamin C in Elderly Women." Journal of Nutrition (1998), vol. 128, No. 12, pp. 2383-2390.

Sujatha et al. "Modulation of Lipid Peroxidation by Dietary Components." Toxicol In Vitro (1995), vol. 9, No. 3, pp. 231-236.

Office Action dated Jan. 20, 2010 for the corresponding Japanese Patent Application No. 2005-5202355.

* cited by examiner

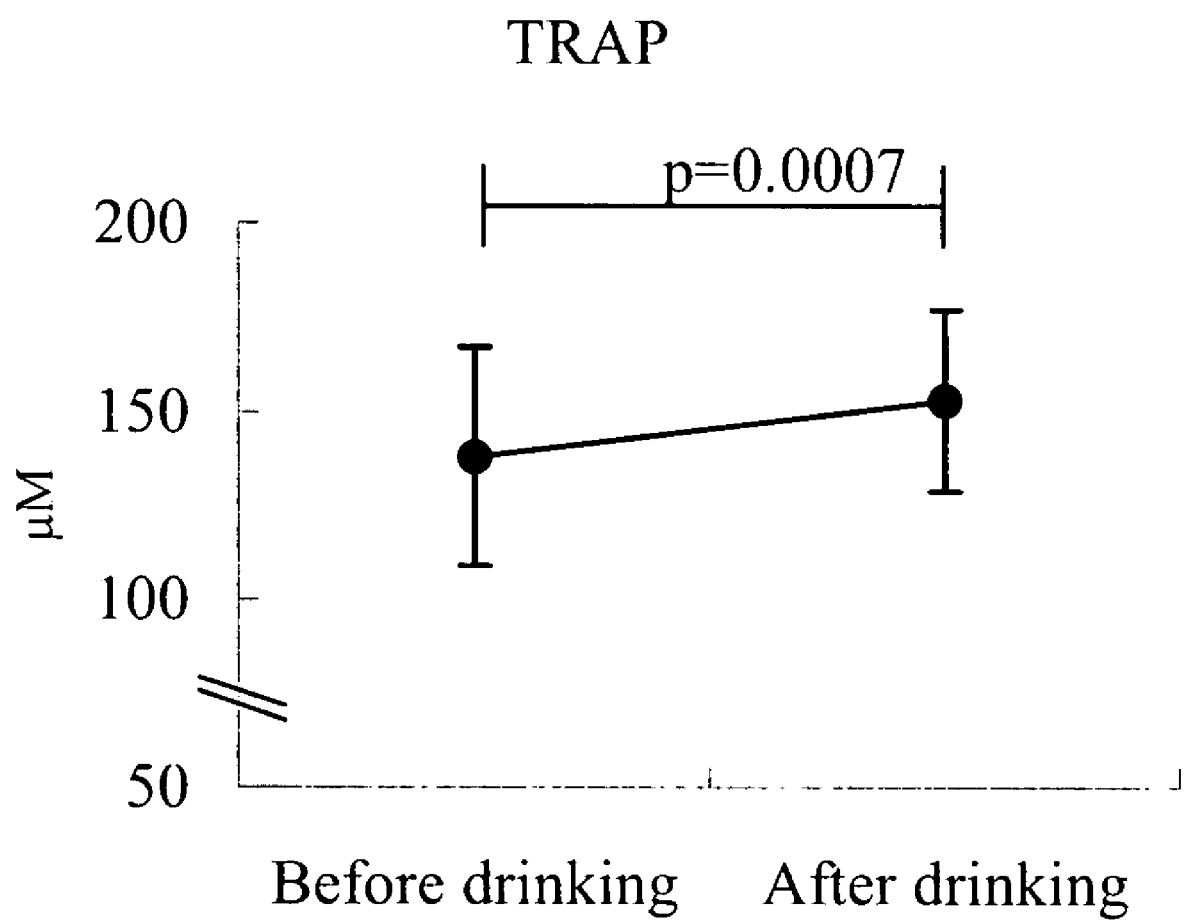

METHOD OF ENHANCING BLOOD ANTIOXIDANT ACTIVITY INGESTING A COMPOUND IN THE FORM OF AT LEAST ONE FORM SELECTED FROM AMONGST JUICE, POWDER, GRANULE, TABLET AND CAPSULE, WHICH CONTAINS AN EFFECTIVE AMOUNT OF AT LEAST ONE VEGETABLE SELECTED FROM THE GROUP CONSISTING OF BROCCOLI, SPINACH, PARSLEY, *KOMATSUNA* (*BRASSICAD RAPA* L.) AND JAPANESE RADISH LEAVES, AND AT LEAST ONE VEGETABLE SELECTED FROM AMONGST LETTUCE, CABBAGE AND CELERY

This Application is the National Phase of International Application No. PCT/JP2003/015572 filed Dec. 5, 2003, and claims the priority from Japanese Application No. 2002-354919, filed Dec. 6, 2002, and from Japanese Application No. 2003-101496, filed Apr. 4, 2003, the complete disclosures of which are incorporated herein by reference.

TECHNICAL FIELD

The present invention relates to food compositions containing a green-yellow vegetable and a light-colored vegetable, pharmaceutical preparations and methods comprising ingesting these vegetables.

BACKGROUND OF THE INVENTION

Recent studies have revealed that lipid peroxides generated in the body cause various diseases. Therefore, various foods and pharmaceutical preparations for inhibiting lipid peroxide generation have been proposed (e.g., Japanese Unexamined Patent Publication No. 2000-198740).

In diabetic patients, active oxygen-induced blood and tissue disorders progress with increasing blood sugar. Such oxidation stress is known to cause the onset or aid the progress of complications such as arteriosclerosis and capillary disorders. Therefore, a method for preventing or treating diabetic complications by using antioxidants has been sought with the expectation of improving the oxidation state of blood and tissues.

DISCLOSURE OF THE INVENTION

Objects of the invention are to: inhibit the generation of blood lipid peroxides; increase vitamin E levels; enhance antioxidant activity; and prevent or treat diabetic complications.

The inventors of the present invention found that ingestion of a green-yellow vegetable and a light-colored vegetable is effective for achieving the above objects and accomplished the invention.

The present invention provides the following compositions and methods.

1. A composition comprising a green-yellow vegetable and a light-colored vegetable.
2. A composition according to item 1 wherein the green-yellow vegetable is at least one member selected from the group consisting of broccoli, spinach, parsley, komatsuna (*Brassica rapa* L.), Japanese radish leaves, and carrot, and the light-colored vegetable is at least one member selected from the group consisting of lettuce, cabbage, celery, and yam (*Dioscorea japonica*).
3. A composition according to item 1 wherein the weight ratio of green-yellow vegetable to light-colored vegetable is about 1:1 to about 1:3, calculated as raw vegetable.
4. A composition according to item 1, further comprising at least one member selected from the group consisting of bilberry extract, coenzyme Q10, astaxanthin, tocotrienol, pycnogenol, tea polyphenols, grape seed extract, methyl hesperidin, and brown rice powder.
5. A composition according to item 1 which is a food.
6. A composition according to item 1 which is a food for inhibiting the generation of blood lipid peroxides.
7. A composition according to item 1 which is a food for lowering blood TBARS levels or suppressing an elevation of blood TBARS levels.
8. A composition according to item 1 which is a food for increasing blood vitamin E levels.
9. A composition according to item 1 which is a food for enhancing blood antioxidant activity.
10. A composition according to item 1 which is a food for lowering blood active oxygen levels or suppressing an elevation of blood active oxygen levels.
11. A composition according to item 1 which is a food for preventing or treating diabetic complications.
12. A composition according to item 1 which comprises therapeutically effective amounts of green-yellow vegetable and light-colored vegetable, the composition being a lipid peroxide generation inhibitor.
13. A composition according to item 1 which comprises therapeutically effective amounts of green-yellow vegetable and light-colored vegetable, the composition being a blood TBARS level lowering agent or a blood TBARS level elevation suppressing agent.
14. A composition according to item 1 which comprises therapeutically effective amounts of green-yellow vegetable and light-colored vegetable, the composition being a blood vitamin E level increasing agent.
15. A composition according to item 1 which comprises therapeutically effective amounts of green-yellow vegetable and light-colored vegetable, the composition being a blood antioxidant activity enhancer.
16. A composition according to item 1 which comprises therapeutically effective amounts of green-yellow vegetable and light-colored vegetable, the composition being a blood active oxygen level lowering agent or a blood active oxygen level elevation suppressing agent.
17. A composition according to item 1 which comprises therapeutically effective amounts of green-yellow vegetable and light-colored vegetable, the composition being a preventive agent for preventing or a therapeutic agent for treating diabetic complications.
18. A method of inhibiting the generation of blood lipid peroxides, which comprises ingesting effective amounts of a green-yellow vegetable and a light-colored vegetable.
19. A method for lowering blood TBARS levels or suppressing an elevation of blood TBARS levels, which comprises ingesting effective amounts of a green-yellow vegetable and a light-colored vegetable.
20. A method of increasing blood vitamin E levels, which comprises ingesting effective amounts of a green-yellow vegetable and a light-colored vegetable.
21. A method of enhancing blood antioxidant activity, which comprises ingesting effective amounts of a green-yellow vegetable and a light-colored vegetable.
22. A method for lowering blood active oxygen levels or suppressing an elevation of blood active oxygen levels, which comprises ingesting effective amounts of a green-yellow vegetable and a light-colored vegetable.

23. A method of preventing or treating diabetic complications, which comprises ingesting effective amounts of a green-yellow vegetable and a light-colored vegetable.

The present invention is described below in detail.

The composition of the invention can suppress an elevation in blood TBARS (Thiobarbituric Acid Reactive Substances) levels, or lower blood TBARS levels. TBARS levels are generally used as an indicator of the amount of lipid peroxides generated. Thus it can be said that the composition of the invention, which suppresses the elevation of or lowers TBARS levels, can suppress the elevation of blood lipid peroxide levels or lower blood lipid peroxide levels.

The generation of lipid peroxide is associated with various diseases such as diabetic complications, in particular diabetic vascular complications (e.g., retinopathy, nephropathy, neurosis, cataract, coronary artery diseases, periodontosis, gangrene, cholelithiasis, infectious diseases) (see, for example, J. Periodont. Res. 1996; 31:508-515, Advanced glycation endoproducts (AGEs) induce oxidant stress in the gingiva: a potential mechanism underlying accelerated periodontal disease associated with diabetes). Thus the composition of the invention is expected to exhibit preventive or therapeutic effects for such lipid peroxide generation-related diseases.

The composition of the invention has the action of increasing blood vitamin E levels. The administration of vitamin E is effective for inhibiting the onset or progress of diabetic vascular complications (for example, retinal blood flow is improved by administering vitamin E; Japan Medical Association Journal, vol. 124, No. 11/Dec. 1, 2000). Therefore, the intake or administration of the composition of the invention is expected to prevent or treat such diabetic vascular complications.

The composition of the invention has the action of enhancing blood total antioxidant activity. In this specification, "enhancing" refers to inhibition of reduction as well as to enhancement. The composition and pharmaceutical preparation of the invention, which have the action of enhancing blood TRAP (Total Radical Trapping Antioxidant Activity) levels, are capable of enhancing blood total antioxidant activities, in particular. It is known that as TRAP levels rise, the risk of diabetic complications is reduced. Thus substances having a TRAP level-increasing action are useful to prevent or treat diabetic complications (Fava D. et al., Diabete Med., 2002 September, 19(9), 752-7; Ceriello A et al., Eur. J. Invest., 2001 April, 31(4), 322-8; Ceriello A. et al, Metabolism, 1999 December, 48(12), 1503-8).

TRAP levels can be determined according to the Rice-Evans method (Rice-Evans C. et al., Total antioxidant status in plasma and body fluids, Methods in Enzymology, 234, 279-293, 1994).

Total antioxidant activity includes antioxidant activity of vitamin E. Thus the total antioxidant activity, which correlates with vitamin E levels, also reflects antioxidant activities of substances other than vitamin E, and is used as an indicator of total antioxidant effect. Since the antioxidant activity enhancement of the composition of the invention is higher than antioxidant activity based on vitamin E level-increasing action, not only the vitamin E level-increasing action of the composition but also antioxidant activity based on other factors appears to contribute to the antioxidant activity-enhancing action of the composition of the invention.

It is generally known that vitamin E inhibits the generation of active oxygen. It is also known that the presence of active oxygen is a factor in lipid peroxide generation. The composition of the invention, which has vitamin E level-increasing action and TBARS level-lowering or elevation-suppressing action, has the action of decreasing active oxygen or inhibiting an increase in active oxygen.

The methods of the invention are also based on the above-mentioned actions of the composition of the invention.

The compositions, pharmaceutical preparations, and methods of the invention have the following effects:
(1) inhibiting the generation of blood lipid peroxide;
(2) lowering blood TBARS levels or suppressing an elevation of blood TBARS levels or;
(3) increasing blood vitamin E levels;
(4) enhancing blood antioxidant activities;
(5) enhancing blood TRAP levels;
(6) lowering blood active oxygen levels or suppressing an elevation of blood active oxygen levels; and
(7) preventing or treating diabetic complications.

The composition of the invention can be used as a food for persons who require such effects (e.g., a health food, functional food, food for specified health use, food for patients with eating disorders), or as a pharmaceutical preparation.

The composition of the invention can be used as a pharmaceutical preparation such as a lipid peroxide generation inhibitor; a blood TBARS level lowering agent or a blood TBARS level elevation suppressing agent; a blood vitamin E level increasing agent; a blood antioxidant activity enhancer; a blood active oxygen level-lowering agent or a blood active oxygen level elevation suppressing agent; or a preventive agent for preventing or a therapeutic agent for treating diabetic complications.

The composition of the invention comprises a green-yellow vegetable and a light-colored vegetable. Green-yellow vegetables contain at least 600 µg of carotene per 100 g of raw vegetable. Although the carotene content of tomatoes is less than 600 µg, tomatoes are also categorized as green-yellow vegetables because they are generally ingested in large amounts. Examples of green-yellow vegetables usable in the invention include broccoli, kale, spinach, komatsuna (*Brassica rapa* L.), Japanese radish leaves, parsley, brussels sprouts, takana (*Brassica juncea* Czern. et Coss. var. *integrifolia* Sinsk.), karashina (*Brassica juncea* Czern. et Coss.), Japanese basil, tomato, carrot, squash, garland chrysanthemum, taisai, sweet pepper and the like. Among these, broccoli, spinach, komatsuna (*Brassica rapa* L.), parsley and Japanese radish leaves are preferable. Green-yellow vegetables can be used singly or in combination of two or more.

Light-colored vegetables refer to vegetables other than green-yellow vegetables. Example of light-colored vegetables usable in the invention include cauliflower, lettuce, cabbage, celery, Chinese cabbage, turnip, Japanese radish, Japanese horseradish, onion, bitter melon, garlic, yam (*Dioscorea japonica*) and the like. Among these, lettuce, cabbage and celery are preferable. Light-colored vegetables can be used singly or in combination of two or more.

The combination of a green-yellow vegetable and a light-colored vegetable is preferably a combination of a green-yellow vegetable as mentioned above and a light-colored vegetable as mentioned above. Specific examples of such combinations include a combination of at least one of broccoli, spinach, parsley, komatsuna (*Brassica rapa* L.), Japanese radish leaves, and carrot, and at least one of lettuce, cabbage, celery and yam (*Dioscorea japonica*); and a combination of at least one of broccoli, spinach, parsley, komatsuna (*Brassica rapa* L.), and Japanese radish leaves, and at least one of lettuce, cabbage and celery. More specifically, broccoli can be used as a green-yellow vegetable, and cabbage as a light-colored vegetable. If necessary, at least one of spinach, parsley, komatsuna (*Brassica rapa* L.), Japanese radish leaves, lettuce and celery may be added. Specific examples of such combinations are a combination of broccoli, cabbage, celery, and Japanese radish leaves; a combination of broccoli, cabbage, lettuce, and komatsuna (*Brassica rapa* L.), and a combination of broccoli, cabbage, spinach, and parsley.

More specifically, a combination containing broccoli, cabbage, spinach, parsley, komatsuna (*Brassica rapa* L.), Japanese radish leaves, lettuce, and celery is particularly preferable.

The composition of the invention preferably contains green-yellow vegetable-derived substances and light-colored vegetable-derived substances in a proportion (weight ratio) such that the green-yellow vegetable-derived substance: light-colored vegetable-derived substance ratio is from about 1:1 to about 1:3, and preferably from about 1:1.5 to about 1:2, when calculated as raw vegetables.

When the composition contains broccoli, cabbage, spinach, parsley, komatsuna (*Brassica rapa* L.), Japanese radish leaves, lettuce and celery, the composition preferably comprises, as percentages of the total weight of vegetables, about 5 to 30 wt. % of broccoli, about 15 to 35 wt. % of cabbage, about 0.1 to 20 wt. % of spinach, about 0.01 to 10 wt. % of parsley, about 0.01 to 10 wt. % of komatsuna (*Brassica rapa* L.), about 0.01 to 10 wt. % of Japanese radish leaves, about 1 to 25 wt. % of lettuce, and about 1 to 25 wt. % of celery, calculated as the raw vegetables.

The usually eaten parts of green-yellow vegetables and light-colored vegetables are utilized in the invention, unless otherwise specified.

In the invention, the vegetables may be crushed in order to use the resultant product as a whole. For example, vegetable purees may be used. Alternatively, vegetables may be crushed or squeezed in order to use only the vegetable juices obtained. Filtrates obtained by filtering the crushed substances or vegetable juices, and supernatants obtained by centrifugation of such filtrates are also usable. Vegetable juices may be used in the form of concentrates. Concentrates may be dried and processed into powders, granules, tablets, capsules and like products and used in such a form.

Thus, green-yellow vegetables and light-colored vegetables that are processed by a combination of known operations such as washing, peeling, coring, crushing, squeezing, filtration, separation, concentration, heating, cooling and drying are usable in the invention.

The composition of the invention comprises a green-yellow vegetable and a light-colored vegetable. The composition may consist solely of such vegetables (100% vegetables), or may contain other ingredients.

Ingredients other than green-yellow vegetables and light-colored vegetables that may be optionally incorporated into the composition of the invention are not particularly limited, so long as the effects of the invention are not impaired. Examples of usable ingredients are ingredients typically incorporated according to the form and purpose of the composition, for example, those incorporated into foods, pharmaceuticals, or compositions for oral cavity use.

It is particularly preferable to incorporate into the composition of the invention at least one member selected from the group consisting of bilberry extract, coenzyme Q10, astaxanthin, tocotrienol, pycnogenol, tea polyphenol, grape seed extract, methyl hesperidin and brown rice powder because these advantageously enhance the above-mentioned effects. The amount of such optional ingredients is usually about 0.0002 to 0.65 wt. %, and preferably about 0.0004 to 0.25 wt. %, based on the total weight of vegetables and fruits in the composition, calculated as raw vegetables and fruits, but is not limited to these ranges.

The adult daily intake of such optional ingredients other than brown rice powder in the composition of the invention is usually about 1 to 1000 mg, and preferably about 2 to 400 mg. The adult daily intake of brown rice powder is usually about 0.1 to 50 g, and preferably about 1 to 30 g.

Bilberry extract, an optional ingredient, is not particularly limited as long as the effects of the invention can be achieved. Bilberry extract can be obtained, for example, by immersing bilberry (*Vaccinium myrtillus*) fruits in water or a hydrophilic organic solvent such as alcohol, ether or acetone, followed by extraction.

Grape seed extract, an optional ingredient, is not particularly limited as long as the effects of the invention can be achieved. Grape seed extract is an extract which may be derived from the seeds of European grape (*Vitis vinifera*) by methods described in Japanese Examined Patent Publication No. 31208/1994, Japanese Unexamined Patent Publications Nos. 162685/1988 and 200781/1991, 48593/1990 and 9909/1991, etc., the extract containing proanthocyanidin and anthocyanoids.

Pycnogenol, an optional ingredient, is a French maritime pine (*Pinus pinaster*) bark extract. Pycnogenol is not particularly limited as long as the effects of the invention can be achieved. Pycnogenol can be obtained, for example, by extracting French maritime pine bark in water or an aqueous organic solvent mixture (or hydrophilic organic solvent) such as ethanol/water.

Brown rice powder, an optional ingredient, preferably has a particle diameter of 10 to 200 μm.

Examples of ingredients other than green-yellow vegetables, light-colored vegetables, and the above-mentioned optional ingredients that can be incorporated into the composition of the invention include fruits such as apples, lemons, mandarins, grapefruits, pineapples, bananas, grapes, peaches, melons, plums, and Japanese plums (ume). Such fruits can be processed in a manner similar to green-yellow vegetables and light-colored vegetables for use. When the composition of the invention comprises ingredients other than vegetables, the amount of other ingredients is not particularly limited so long as the effects of the invention are not impaired. The amount can be decided according to the intended use and form of the composition. For example, when the composition comprises fruit, the amount of fruit calculated as raw fruit is preferably about 80 wt. % or less, and particularly about 20 to 50 wt. %, of the total weight of vegetables and fruit in the composition, calculated as raw vegetables and raw fruit.

Additives commonly used in preparation of foods may be incorporated into the food of the invention, as long as they do not impair the effects of the invention. Specific examples of usable additives include excipients, sweeteners, thickeners, vitamins, colorants and aromatic substances.

When the food of the invention comprises ingredients other than vegetables, the amount of such other ingredients is not particularly limited as long as the effects of the invention are not impaired. The amount can be suitably decided according to the form of the food and other factors. When the food of the invention comprises additives, the amount of additives is not particularly limited and can be suitably selected according to the form of the food, etc. The composition may comprise, for example, about 50 wt. % or less of additives, based on the total weight of the composition. When the composition is in a liquid form (e.g., a liquid beverage such as vegetable juice, vegetable/fruit blended beverage, or mixed fruit/vegetable juice), the composition may comprise about 20 wt. % or less of ingredients other than vegetables, based on the total weight of the composition. When the composition is in a semi-solid or solid form, the composition may comprise about 50 wt. % or less of ingredients other than vegetables, based on the total weight of the composition.

The form of the food in the invention is not particularly limited. Examples thereof include foods, beverages and other comestibles. Specific examples include powders, tablets, chewable tablets, capsules, candies, jellies, biscuits, cakes, breads, noodles and like solid or semi-solid foods; vegetable juices, vegetable/fruit blended beverages, mixed fruit/vegetable juices, and like liquid beverages; and sauces (tare), dressings, Worcester sauces, soy sauces, and like seasonings. Among these, a liquid beverage, in particular a vegetable juice, is preferable as the form of the food of the invention. Such food products can be prepared by conventional methods selected according to the form of the food.

The intake amount of the food of the invention is not particularly limited and can be suitably decided according to the form of the food, the age, body weight and sex of the person taking the food, purpose of intake, and other factors. The food can be ingested in such an amount that the adult daily intake of the green-yellow vegetables and light colored vegetables per kg body weight is about 0.5 to 15 g, preferably about 1 to 10 g, and more preferably about 2 to 6 g, calculated as raw vegetables, and can be ingested once per day or divided into 2 to 4 servings.

When the composition of the invention is a pharmaceutical composition, ingredients other than green-yellow vegetables and light-colored vegetables may be incorporated, so long as they do not impair the effects of the invention. Examples of usable other such ingredients are additives conventionally used in the production of pharmaceutical preparations, such as excipients, expanders, binders, wetting agents, disintegrators, surfactants, lubricants, dispersants, buffers, preservatives, solubilizers, anticeptics, flavoring/aromatic agents, and stabilizers. The amounts of such additives are not particularly limited so long as the contemplated effects are not impaired. The amount can be suitably selected according to the kind(s) of additive(s), dosage form of the pharmaceutical composition, etc.

When the pharmaceutical composition is in the form of a liquid, the composition may comprise about 0.01 to 20 wt. % of ingredients other than vegetables, based on the total weight of the composition. When the pharmaceutical composition is in the form of a solid or semi-solid form, the composition may comprise about 0.01 to 50 wt. % of non-vegetable ingredients, based on the total weight of the composition.

The dosage unit form of the pharmaceutical composition can be selected from a variety of forms according to the intended therapy. Examples of dosage forms include tablets, pills, granules, capsules, troches and like solid preparations; medical powders (or powder preparations) for internal use, medical powders for external use, powders and like powder preparations; solutions, suspensions, emulsions, syrups, lotions, aerosols, infusions, decoctions and like fluid preparations; ointments and like cream preparations; and cataplasms. The pharmaceutical preparation of the invention can be produced by conventional processes according to the intended form of preparation.

The method of administration of the pharmaceutical preparation is not particularly limited. The preparation may be administered, for example, orally or transdermally, according to the form of the preparation, the age, sex and other characteristics of the patient, the severity of the disease, and other factors. The dosage is preferably such that the adult daily intake of vegetables per kg of body weight is about 0.5 to 15 g, preferably about 1 to 10 g, more preferably about 2 to 6 g, calculated as raw vegetables. The pharmaceutical composition can be administered once per day or divided into several doses.

When the composition of the invention is a composition for oral cavity use, additives commonly used in compositions for oral cavity use may be incorporated as long as they do not impair the effects of the invention. Examples of usable additives include excipients, sweeteners, thickeners, vitamins, colorants and flavoring/aromatic agents. The amount of additives used is not particularly limited and can be suitably selected according to the kind(s) of additive(s), form of the composition, etc.

The form of the composition for oral cavity use of the invention is not particularly limited. Examples thereof include dentifrices, mouth washes, troches, and oral pastes. Such compositions for oral cavity use can be prepared by conventional production methods according to the intended form of the composition.

When the composition for oral cavity use is in the form of a liquid, the composition may comprise about 0.01 to 20 wt. % of ingredients other than vegetables, based on the total weight of the composition. When the composition is in the form of a solid or semi-solid form, the composition may comprise about 0.01 to 50 wt. % of non-vegetable ingredients, based on the total weight of the composition.

The composition for oral cavity use of the invention can be used according to standard methods depending on the form of the composition.

The amount of the composition for oral cavity use of the invention is not particularly limited and can be suitably determined according to the form of the composition, the age, body weight and sex of the person taking the composition, purpose of use, and other factors. The composition can be used in such an amount that adult daily intake of green-yellow vegetables and light-colored vegetables per kg body weight is about 0.5 to 15 g, preferably about 1 to 10 g, and more preferably about 2 to 6 g, calculated as raw vegetables, and it can be taken once per day or divided into 2 to 4 doses.

BRIEF DESCRIPTION OF THE DRAWINGS

FIG. 3 is a diagram showing the changes in blood TRAP levels in Test Example 2.

BEST MODE FOR CARRYING OUT THE INVENTION

The present invention is described below in more detail with reference to Examples. The invention, however, is not limited thereto.

EXAMPLE 1

The ingredients shown below in Table 1 were mixed to prepare a vegetable juice (160 g per can).

TABLE 1

| Component | (wt. %) |
|---|---|
| Broccoli puree | 10 |
| Celery juice | 15 |
| Lettuce juice | 15 |

TABLE 1-continued

| Component | (wt. %) |
|---|---|
| Cabbage juice | 20 |
| Spinach juice | 10 |
| Parsley juice | 5 |
| Komatsuna | 1 |
| Japanese radish leaves | 1 |
| Water | balance |
| Total | 100 |

The green-yellow vegetable:light-colored vegetable ratio, calculated as raw vegetables, was 25.5:45.

TEST EXAMPLE 1

Fourteen adult males with type 2 diabetes were instructed to drink one can (160 g) of the vegetable juice obtained in Example 1 before each meal (3 cans per day) for 2 weeks.

Figure 1:
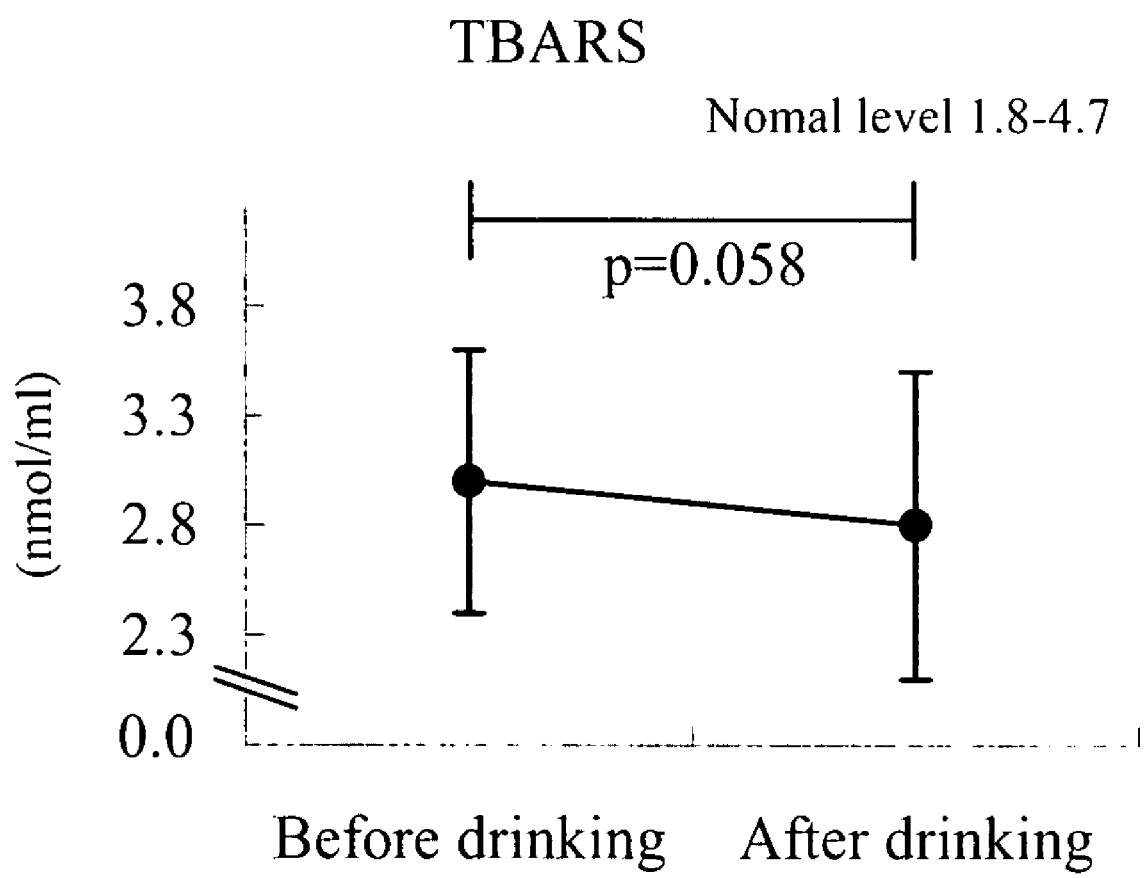
FIG. 1 is a diagram showing the changes in blood TBARS levels in Test Example 1.
Figure 2:
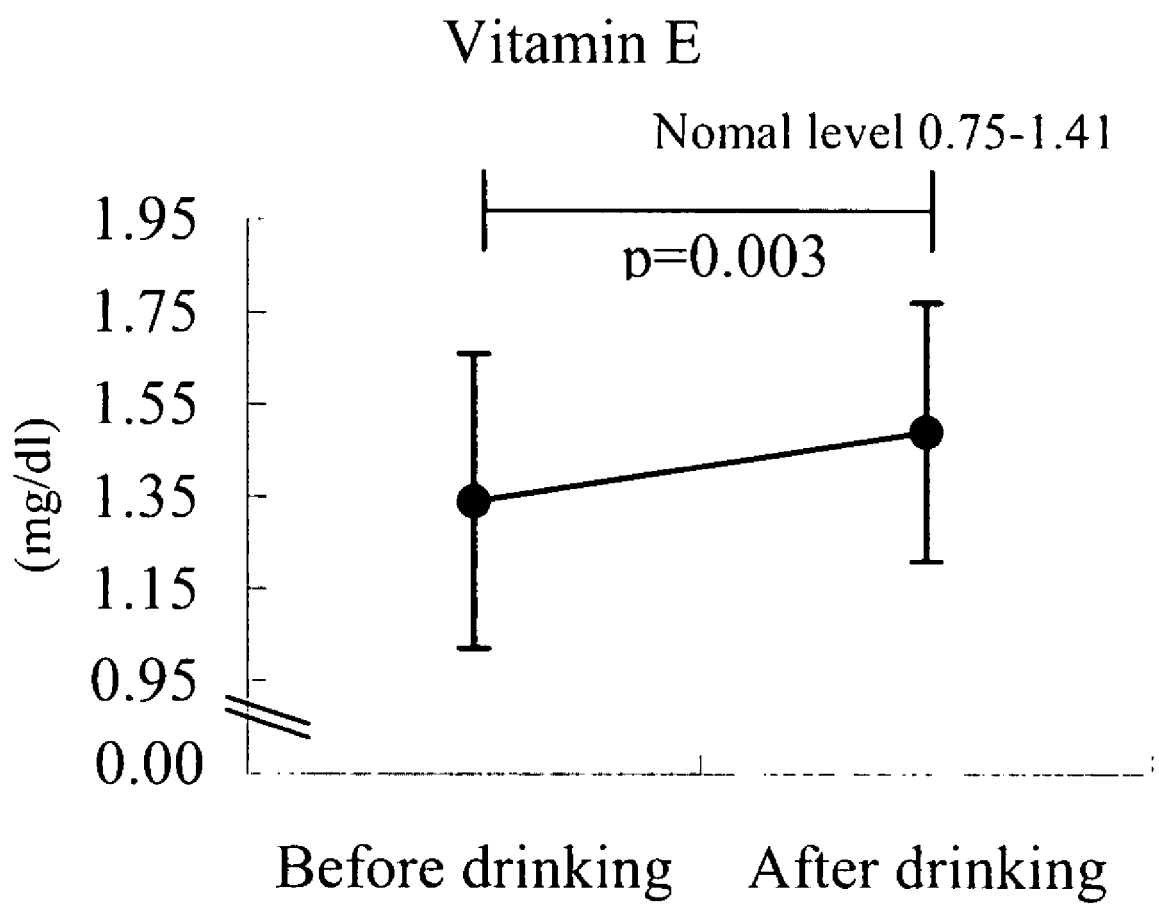
FIG. 2 is a diagram showing the changes in blood vitamin E levels in Test Example 1.

The blood TBARS levels and blood vitamin E levels were measured before and after drinking. The TBARS levels were determined according to the TBA method (Thiobarbituric Acid Method, Kunio Yagi, Vitamin 49, 403-405, 1975). The vitamin E levels were determined according to the fluorescence method (Koichi Abe et al., Nutrition and Food 28, 277-280, 1975). FIGS. 1 and 2 show the results.

The results show that the blood TBARS levels were reduced by drinking the vegetable juice, i.e., food of the invention (a significant difference was observed). Diabetic patients drank the vegetable juice in this test. Therefore, the results clearly show that drinking the vegetable juice of the invention has the effect of reducing TBARS levels of diabetic patients (persons with high blood sugar). The results also show that blood vitamin E levels can be increased by drinking the vegetable juice of the invention (a significant difference was observed). Diabetic patients drank the vegetable juice in this test. Therefore, the results clearly show that drinking the vegetable juice of the invention has the effect of increasing vitamin E levels of diabetic patients (persons with high blood sugar).

TEST EXAMPLE 2

In a manner similar to Test Example 1, fourteen adult males with type 2 diabetes were instructed to drink one can (160 g) of the vegetable juice obtained in Example 1 before each meal (3 cans per day) for 2 weeks. The blood TRAP levels were measured before and after drinking. The TRAP levels were measured using an absorption meter according to the manual method with reference to the Rice-Evans method (Rice-Evans C, et al.: Total antioxidant Status in plasma and body fluids, Methods in Enzymology, 234, 279-293, 1994).

The following substances (1) to (4) were placed in a 1 ml absorption meter cuvette and mixed. Trolox (6-hydroxy-2,5, 7,8-tetramethylchroman-2-carboxylic acid), which is known to have potent antioxidant activity, was used as a positive control.

(1) 25 µl of a blood serum sample obtained from each subject or 25 µl of 400 µM trolox (6-hydroxy-2,5,7,8-tetramethyl-chroman-2-carboxylic acid)
(2) 36 µl of metmyoglobin (3) 300 µl of 500 µM ABTS (2,2'-azinobis(3-ethylbenzothiazoline-6-sulfonic acid), diammonium salt)
(4) 472 µl of 0.1 mM DTPA (dietylenetriamine pentaacetic acid)-containing PBS buffer solution Subsequently, 167 µl of 450 µM $H_2O_2$ was added and absorbance was measured over time (25° C., 734 nm). The time (min.) required from the $H_2O_2$ addition to increase the absorbance to 735 nm (time until oxidation of metmyoglobin starts) was calculated. The calculated time was substituted in the following formula to calculate the retention activity (TRAP) of the blood serum sample.

Retention activity of blood serum sample (µM)=(400 µM * time required for the sample (min.)/time required for Trolox (min.))

FIG. 3 shows the retention activity of each blood serum sample. As shown in FIG. 3, the TRAP levels increased after drinking the vegetable juice for 2 weeks, which indicates that antioxidant activity in the subjects was enhanced by drinking the vegetable juice. The correlation of vitamin E levels and TRAP levels for each patient was calculated using Spearman's formula. The result was R=0.165, which suggests that not only the increase of vitamin E levels but also other factors are involved in the elevation of TRAP levels.

FOOD EXAMPLES

The components shown in Tables 2 and 3 below were mixed to prepare vegetable juices (160 g per can).

TABLE 2

| Component | Food Example 1 (wt. %) | Food Example 2 (wt. %) | Food Example 3 (wt. %) | Food Example 4 (wt. %) | Food Example 5 (wt. %) |
|---|---|---|---|---|---|
| Broccoli puree | 20 | 15 | 10 | 20 | 15 |
| Celery juice | 10 | 15 | 15 | 10 | 15 |
| Lettuce juice | 15 | 10 | 15 | 15 | 10 |
| Cabbage juice | 15 | 20 | 20 | 15 | 20 |
| Spinach juice | 10 | 5 | 10 | 10 | 5 |
| Parsley juice | 5 | 10 | 5 | 5 | 10 |
| komatsuna | 1 | 2 | 1 | 1 | 2 |
| Japanese radish leaves | 1 | 2 | 1 | 1 | 2 |
| Tea polyphenols | 0.05 | — | — | — | — |
| Bilberry extract | — | 0.1 | — | — | — |
| Astaxanthin | — | — | 0.05 | — | — |
| Coenzyme Q10 | — | — | — | 0.05 | — |
| Tocotrienol | — | — | — | — | 0.1 |
| Water | Balance | Balance | Balance | Balance | Balance |
| Total | 100 | 100 | 100 | 100 | 100 |

TABLE 3

| Component | Food Example 6 (wt. %) | Food Example 7 (wt. %) | Food Example 8 (wt. %) | Food Example 9 (wt. %) | Food Example 10 (wt. %) |
|---|---|---|---|---|---|
| Broccoli puree | 10 | 15 | 10 | 20 | 15 |
| Celery juice | 15 | 15 | 15 | 10 | 15 |
| Lettuce juice | 15 | 10 | 15 | 15 | 10 |
| Cabbage juice | 20 | 20 | 20 | 15 | 20 |
| Spinach juice | 10 | 5 | 10 | 10 | 5 |
| Parsley juice | 5 | 10 | 5 | 5 | 10 |
| Komatsuna | 1 | 2 | 1 | 1 | 2 |
| Japanese radish leaves | 1 | 2 | 1 | 1 | 2 |
| Pycnogenol | 0.05 | — | — | — | 0.1 |
| Grape seed extract | — | 0.1 | — | 0.05 | — |
| methyl hesperidin | — | — | 0.2 | — | — |
| Tea polyphenols | — | — | — | 0.05 | — |
| Coenzyme Q10 | — | — | — | — | 0.05 |
| Water | Balance | Balance | Balance | Balance | Balance |
| Total | 100 | 100 | 100 | 100 | 100 |

The invention claimed is:

1. A method of enhancing blood antioxidant activity in a subject comprising ingesting by said subject at least one composition in at least one form selected from the group consisting of a juice, powder, granule, tablet, or capsule, said composition comprising an effective amount of broccoli, cabbage, spinach, parsley, komatsuna (*Brassica rapa* L.), Japanese radish leaves, lettuce, and celery, wherein the composition comprises, as a percentage of the total weight of vegetables, about 5-30 wt. % of broccoli, about 15-35 wt. % of cabbage, about 0.1-20 wt. % of spinach, about 0.01-10 wt. % of parsley, about 0.01-10 wt. % of Japanese radish leaves, about 10-25 wt. % of lettuce, and 1-25 wt. % of celery, calculated as the weight percent of the vegetables when raw.

2. The method according to claim 1, wherein the composition contains green-yellow, vegetable-derived substances and light-colored, vegetable-derived substances, the weight ratio of the green-yellow, vegetable derived substances and the light-colored, vegetable-derived substance being 1:1-1:3, and the green-yellow, vegetable-derived substances consisting of broccoli, spinach, Japanese radish leaves and parsley, and the light-colored, vegetable-derived substance consisting of lettuce, cabbage, and celery.

3. The method according to claim 1, wherein said composition further comprises astaxanthin.

* * * * *